US010413265B2

(12) United States Patent
Stoutenburgh et al.

(10) Patent No.: US 10,413,265 B2
(45) Date of Patent: Sep. 17, 2019

(54) RADIOLOGICAL IMAGING DEVICE WITH ADVANCED SENSORS

(71) Applicant: Epica International, Inc., San Clemente, CA (US)

(72) Inventors: Gregory William Stoutenburgh, San Clemente, CA (US); Damiano Fortuna, Rignano Sul'Arno (IT); Leonardo Manetti, Montevarchi (IT)

(73) Assignee: EPICA INTERNATIONAL., INC., San Clemente, CA (US)

( * ) Notice: Subject to any disclaimer, the term of this patent is extended or adjusted under 35 U.S.C. 154(b) by 0 days.

(21) Appl. No.: 15/366,883

(22) Filed: Dec. 1, 2016

(65) Prior Publication Data

US 2017/0079606 A1    Mar. 23, 2017

Related U.S. Application Data

(63) Continuation of application No. 14/323,808, filed on Jul. 3, 2014, now Pat. No. 9,510,793.

(Continued)

(51) Int. Cl.
*A61B 6/00* (2006.01)
*A61B 6/03* (2006.01)
(Continued)

(52) U.S. Cl.
CPC ............ *A61B 6/5205* (2013.01); *A61B 6/032* (2013.01); *A61B 6/035* (2013.01); *A61B 6/0407* (2013.01);
(Continued)

(58) Field of Classification Search
CPC ......... A61B 6/027; A61B 6/032; A61B 6/035; A61B 6/481; A61B 6/487; A61B 6/547;
(Continued)

(56) References Cited

U.S. PATENT DOCUMENTS

| 4,928,297 A | 5/1990 | Hiroshi et al. |
| 6,940,948 B1 | 9/2005 | Vjatcheslav et al. |

(Continued)

FOREIGN PATENT DOCUMENTS

| CN | 202568283 U | 12/2012 |
| CN | 202982022 U | 6/2013 |

OTHER PUBLICATIONS

CIPO First Office Action dated Nov. 29, 2018 issued in CN Patent Application No. 2015800061718 based on PCT/US2015/011628.
(Continued)

*Primary Examiner* — Hoon K Song
(74) *Attorney, Agent, or Firm* — Steptoe & Johnson LLP (57) ABSTRACT

A radiological imaging device that includes a gantry defining an analysis zone in which at least part of a patient is placed, a source suitable to emit radiation defining a central axis of propagation; a detector suitable to receive the radiation, a translation mechanism adapted to translate the source and the detector in a direction of movement substantially perpendicular to the central axis of propagation; and a control unit adapted to acquire an image from data signals received continuously from the detector while the translation mechanism continuously translates the source emitting the radiation and the detector receiving the radiation, so as to scan the at least part of the patient.

10 Claims, 9 Drawing Sheets

Related U.S. Application Data (60) Provisional application No. 61/932,024, filed on Jan. 27, 2014, provisional application No. 61/932,028, filed on Jan. 27, 2014, provisional application No. 61/932,034, filed on Jan. 27, 2014, provisional application No. 61/944,956, filed on Feb. 26, 2014.

(51) Int. Cl.
*A61B 6/06* (2006.01)
*A61B 6/08* (2006.01)
*A61B 6/04* (2006.01)

(52) U.S. Cl.
CPC .............. *A61B 6/06* (2013.01); *A61B 6/08* (2013.01); *A61B 6/4035* (2013.01); *A61B 6/4233* (2013.01); *A61B 6/487* (2013.01); *A61B 6/542* (2013.01)

(58) Field of Classification Search
CPC ... A61B 6/4233; A61B 6/4266; A61B 6/4417; A61B 6/5205; A61B 6/08; A61B 6/482
See application file for complete search history.

(56) References Cited

U.S. PATENT DOCUMENTS

| | | | |
|---|---|---|---|
| 2004/0013225 A1* | 1/2004 | Gregerson | A61B 6/032 378/19 |
| 2005/0116558 A1 | 6/2005 | Yokoyama et al. | |
| 2008/0118023 A1* | 5/2008 | Besson | A61B 6/06 378/8 |
| 2011/0091017 A1 | 4/2011 | Friedlander et al. | |
| 2012/0189094 A1 | 7/2012 | Neushul et al. | |
| 2013/0058459 A1 | 3/2013 | Desaute | |
| 2013/0343509 A1* | 12/2013 | Gregerson | A61B 6/032 378/4 |

OTHER PUBLICATIONS

Partial European Search Report dated Apr. 15, 2015 in EP 18203695.4.

* cited by examiner

| Input Parameters | | | Output Configuration Paramaters | | | |
|---|---|---|---|---|---|---|
| Imaging Procedure | Tissue / Region of interest | Patient Size | kV | mA | ms | Filter |
| Tomography | Hard / Head | Any | 100 | 30 | 10 | 3 mm Al + 0.2 mm Cu |
| Tomography | Hard / Thorax | Any | 100 | 60 | 5 | 3 mm Al + 0.2 mm Cu |
| Tomography | Soft / Abdomen | Any | 60 | 60 | 10 | 2 mm Al |
| Tomography | Soft / Limbs | Any | 60 | 30 | 15 | 2 mm Al |
| Radiography | Head | Small | 70 | 20 | 10 | 2 mm Al |
| Radiography | Thorax | Small | 80 | 25 | 2 | 2 mm Al |
| Radiography | Abdomen | Small | 75 | 30 | 10 | 2 mm Al |
| Radiography | Limbs | Small | 45 | 30 | 15 | 2 mm Al |
| Radiography | Head | Medium | 80 | 30 | 20 | 2 mm Al |
| Radiography | Thorax | Medium | 85 | 30 | 2 | 2 mm Al |
| Radiography | Abdomen | Medium | 80 | 40 | 10 | 2 mm Al |
| Radiography | Limbs | Medium | 50 | 30 | 20 | 2 mm Al |
| Radiography | Head | Large | 85 | 30 | 20 | 2 mm Al |
| Radiography | Thorax | Large | 95 | 30 | 2 | 2 mm Al |
| Radiography | Abdomen | Large | 90 | 60 | 20 | 2 mm Al |
| Radiography | Limbs | Large | 55 | 30 | 20 | 2 mm Al |
| Fluoroscopy | Head | Small | 70 | 20 | 5 | 2 mm Al |
| Fluoroscopy | Thorax | Small | 80 | 25 | 2 | 2 mm Al |
| Fluoroscopy | Abdomen | Small | 75 | 30 | 5 | 2 mm Al |
| Fluoroscopy | Limbs | Small | 45 | 30 | 5 | 2 mm Al |
| Fluoroscopy | Head | Medium | 80 | 30 | 5 | 2 mm Al |
| Fluoroscopy | Thorax | Medium | 85 | 30 | 2 | 2 mm Al |
| Fluoroscopy | Abdomen | Medium | 80 | 40 | 5 | 2 mm Al |
| Fluoroscopy | Limbs | Medium | 50 | 30 | 5 | 2 mm Al |
| Fluoroscopy | Head | Large | 85 | 30 | 5 | 2 mm Al |
| Fluoroscopy | Thorax | Large | 95 | 30 | 2 | 2 mm Al |
| Fluoroscopy | Abdomen | Large | 90 | 60 | 5 | 2 mm Al |
| Fluoroscopy | Limbs | Large | 55 | 30 | 5 | 2 mm Al |

RADIOLOGICAL IMAGING DEVICE WITH ADVANCED SENSORS

CROSS-REFERENCE TO RELATED APPLICATIONS

This application is a continuation of U.S. patent application Ser. No. 14/323,808, filed Jul. 3, 2014, now U.S. Pat. No. 9,510,793, and claims priority to U.S. Provisional Patent Application No. 61/932,024, filed Jan. 27, 2014; 61/932,028, filed Jan. 27, 2014, 61/932,034, filed Jan. 27, 2014; and 61/944,956, filed Feb. 26, 2014, the contents of which are incorporated herein by reference in their entireties.

BACKGROUND

1. Field

Example aspects herein relate generally to obtaining radiological images, and, more particularly, to a method, system, apparatus, and computer program for performing a total body scan and reconstructing an image of a patient's entire body or an extensive portion thereof.

2. Description of Related Art

Total body radiological imaging devices comprise a bed on which the patient is placed; a so-called gantry having a cavity in which the portion to be analyzed is inserted and suitable to perform the imaging of the patient; and a control station suitable to control the functioning of the device.

In particular, the gantry comprises a source suitable to emit radiation on command, such as X-rays, and a detector suitable to receive the radiation after it has traversed the patient's body and to send a signal suitable to permit the visualization of the internal anatomy of the patient.

Typically, given the need to visualize extensive parts of the body, the detector used is a flat panel sensor, said flat panel sensor having a particularly extensive detection surface, which in some cases exceeds 1600 $cm^2$.

For example, flat panel sensors may be a direct-conversion type, and comprise a panel suitable to receive X-rays emitted by the source and to produce a series of electric charges in response, a segmented matrix of TFT in amorphous silicon which receives the aforementioned electric charges, and an electronic reading system. Flat panel sensors also may be an indirect-conversion type, comprising a layer suitable to receive X-rays emitted by the source and to produce a series of light photons in response (e.g., by scintillation), a segmented matrix of photodetectors (e.g. TFT, CMOS, CCD, and the like) that convert the aforementioned light photons into electric charges, and an electronic reading system. When radiation has struck the entire flat panel sensor, the electronic reading system determines the quantity of electric charge received by each TFT segment in a direct-conversion flat panel sensor or the quantity of electric charge generated by each photodetector of an indirect-conversion type of flat panel sensor, and correspondingly generates a matrix of numbers which represent the digital image.

However, flat panel sensors generally cannot absorb radiation continuously, owing to, for example, the particular interaction between the charges and the segmented matrix of TFT in amorphous silicon. Thus, in order to perform a total body scan of a patient's body, image acquisition of the patient's body is divided into a sequence of two-dimensional images, which are then reconstructed into a total body scan. In particular, reconstruction may require approximating the portions of the body located on edges between two successive images. Furthermore, other portions of the body may have to be reconstructed by approximation of a series of images of those portions. As a result, the use of flat panel sensors in this conventional manner results in poor quality radiological imaging, particularly in the case of total body scanning.

Moreover, the quality of conventional total body scans is also reduced as a result of diffused, so-called parasitic radiation, formed by the interactions between X-rays and matter, which hits the detector and thus degrades the quality of the image. In order to reduce the incidence of parasitic radiation, conventional radiological imaging devices are often fitted with anti-diffusion grids composed of thin lead plates fixedly arranged parallel to each other so as to prevent the diffused rays from reaching the flat panel sensor. However, such grids are only partially effective in remedying the effects of parasitic radiation on image quality. Furthermore, the use of anti-diffusion grids imposes the use of a higher dose, thereby possibly increasing the danger of causing illness.

Moreover, conventional radiological imaging devices are characterized by high production costs and a highly complex construction.

SUMMARY

Existing limitations associated with the foregoing, as well as other limitations, can be overcome by a method for operating a radiological imaging device, and by a system, apparatus, and computer program that operate in accordance with the method.

In one example embodiment herein, a radiological imaging device comprises a gantry defining an analysis zone in which at least part of a patient is placed, a source suitable to emit radiation that passes through the at least part of the patient, the radiation defining a central axis of propagation, a detector suitable to receive the radiation, a translation mechanism adapted to translate the source and the detector in a direction of movement substantially perpendicular to the central axis of propagation, and a control unit. The control unit is adapted to acquire an image from data signals received continuously from the detector while the translation mechanism continuously translates the source emitting the radiation and the detector receiving the radiation, so as to scan the at least part of the patient.

In another example embodiment herein, the detector includes at least one first linear sensor having a first sensitive surface and a second linear sensor having a second sensitive surface, wherein the sensitive surfaces are partially overlapping along the direction of movement. In some example embodiments herein, a superimposition zone corresponding to the overlapping of the sensitive surfaces is positioned substantially at the central axis of propagation.

In some example embodiments herein, the detector includes an inversion unit adapted to rotate at least one of the first linear sensor and the second linear sensor. In a further example embodiment herein, the inversion unit rotates the at least one of the first linear sensor and the second linear sensor in relation to an axis of rotation substantially parallel to the central axis of propagation.

In yet another example embodiment herein, the detector includes at least one flat panel sensor having a radiation sensitive surface and operable in at least a flat panel mode and a linear sensor mode.

In an example embodiment herein, the radiological imaging device further comprises a bed suitable to support the patient and defining an axis of extension. Furthermore, in another example embodiment herein, the direction of movement is substantially parallel to the axis of extension defined by the bed.

In an example embodiment herein, the translation mechanism includes a linear guide.

In yet another example embodiment herein, the radiological imaging device further comprises a rotation mechanism adapted to rotate the source and the detector in relation to the axis of extension. In a further example embodiment herein, the rotation mechanism includes a permanent magnet rotor connected to the source and to the detector.

In an example embodiment herein, the radiological imaging device further comprises a bed suitable to support the patient and defining an axis of extension; a rotation mechanism adapted to rotate the source and the detector in relation to the axis of extension; and at least one positioning laser mounted on the gantry that projects a positioning guidance marker onto the patient; wherein the control unit is adapted to configure, based on received information, at least one of an energy of the radiation and a radiation filter arranged to absorb at least a portion of the radiation before the radiation passes through the at least part of the patient, and wherein the detector includes at least one flat panel sensor having a radiation sensitive surface and operable in at least a flat panel mode and a linear sensor mode.

The radiological imaging device can be useful for performing high quality total body scans with a reduced dosage of radiation. The radiological imaging device also can be constructed with reduced production costs and reduced complexity.

Further features and advantages, as well as the structure and operation of various embodiments herein, are described in detail below with reference to the accompanying drawings.

BRIEF DESCRIPTION OF THE DRAWING

The characteristics of the example embodiments herein are clearly evident from the detailed descriptions thereof, with reference to the accompanying drawings.

FIG. 6b illustrates a perspective view of the gantry subassembly shown in FIG. 6a.

DETAILED DESCRIPTION

With reference to said drawings, reference numeral 1 globally denotes a radiological imaging device. In particular, the radiological imaging device 1 is useful in the medical/veterinary sphere to perform a graphic reconstruction of at least a portion of a patient's body. In one example embodiment herein, the radiological imaging device 1 is suitable to perform a total body scan, that is to say a graphic reconstruction of the whole body or of an extensive portion thereof.

Figure 1:
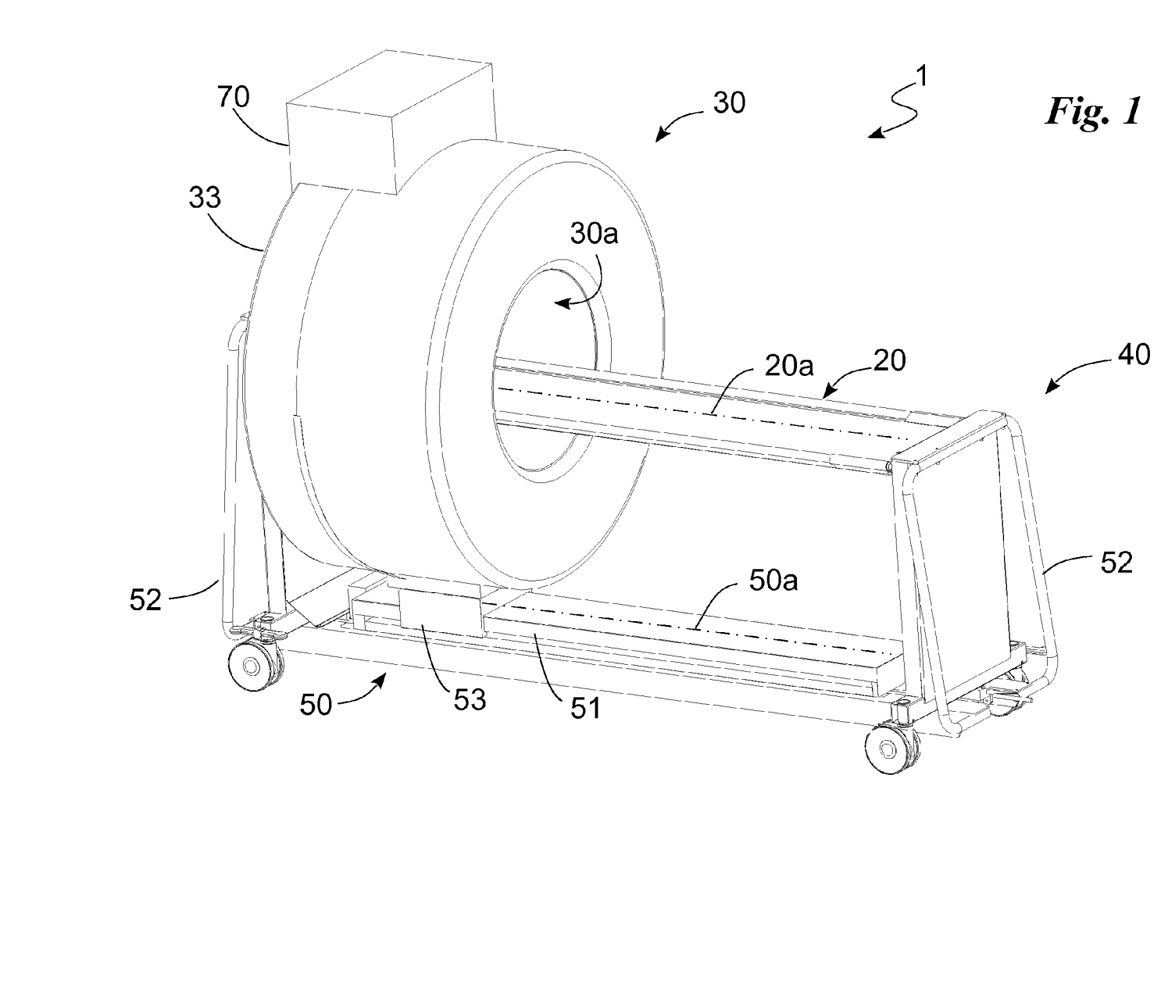
FIG. 1 illustrates a radiological imaging device.
Figure 6A:
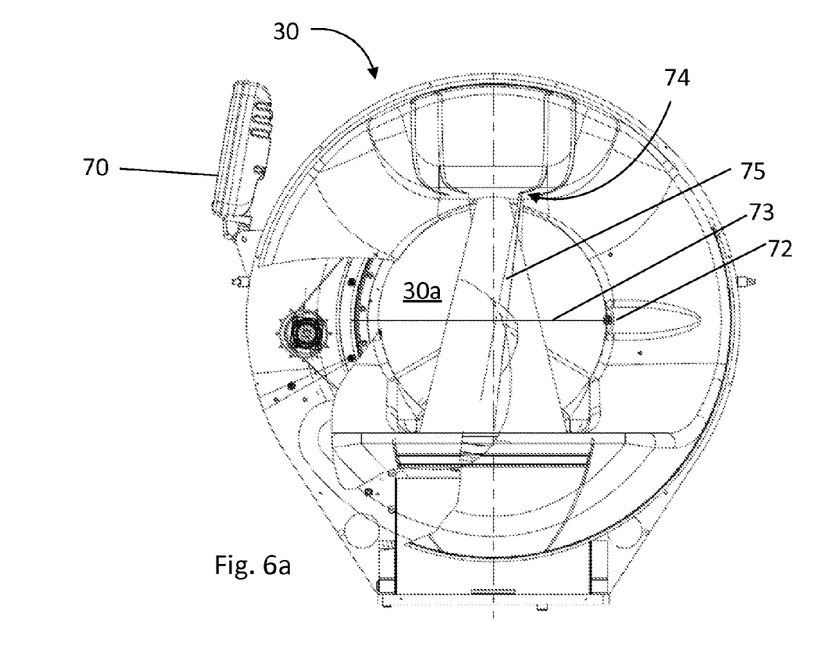
FIG. 6a illustrates a gantry subassembly, with a cut-away portion, according to an example embodiment of the radiological imaging device of FIG. 1.
Figure 6B:
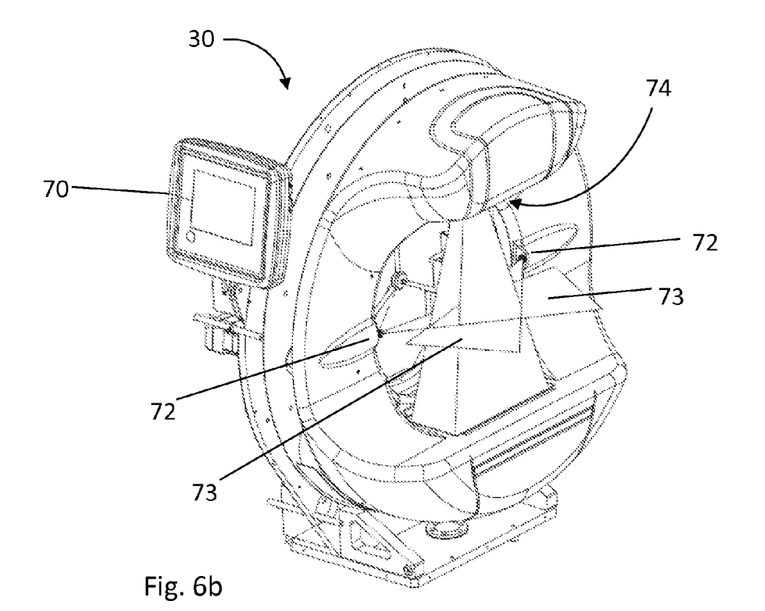

FIG. 1 illustrates an example embodiment of the radiological imaging device 1. The radiological imaging device 1 comprises a bed 20 suitable to support the patient in the correct position and defining a preferred direction of extension 20a; a gantry 30 defining an analysis zone 30a in which at least part of the portion of the patient's body to be imaged is placed and defining a prevailing direction of development, preferably, substantially parallel to the direction 20a; a load-bearing structure 40 suitable to support the bed 20 by way of columns 52 and also suitable to support the gantry 30; a control unit 70 suitable to be placed in data transfer connection with the various components of the radiological imaging device 1; a translation mechanism 50 suitable to move the gantry 30 in a direction of movement 50a; and a rotation mechanism 60 (shown in FIG. 2a) suitable to rotate the gantry 30 around the direction of extension 20a. In one example embodiment, the control unit 70 is mounted to the gantry 30 (as shown in FIGS. 1, 6a, and 6b), although in other examples it can be housed in a stand-alone unit (not shown) such as, for example, a workstation cart, or may formed of multiple parts, such as a first part mounted to the gantry 30 and a second part housed in a stand-alone unit (not shown). These examples are merely illustrative in nature, and in other embodiments, the control unit 70 can be located at other positions and locations besides those described above.

The gantry 30 further comprises a source 31 (FIG. 2a) suitable to emit, in the analysis zone 30a, radiation defining a central axis of propagation 31a; a detector 32 facing the analysis zone 30a so as to receive the radiation after it has traversed the patient's body; and a housing 33 at least partially containing the source 31 and the detector 32. Additionally, in a further example embodiment herein, the gantry 30 further comprises a laser positioning system that includes at least one horizontal laser 72 and at least one vertical laser 74 (FIGS. 6a and 6b). The foregoing subcomponents of the gantry will now be described in turn.

The source 31 is suitable to emit, in a known manner, radiation capable of traversing the body of the patient and interacting with the tissues and fluids present inside said patient. In one example embodiment herein, the source 31 emits, under control of the control unit 70, ionizing radiation, and more particularly, X-rays defining a central axis of propagation 31a.

Figure 2A:
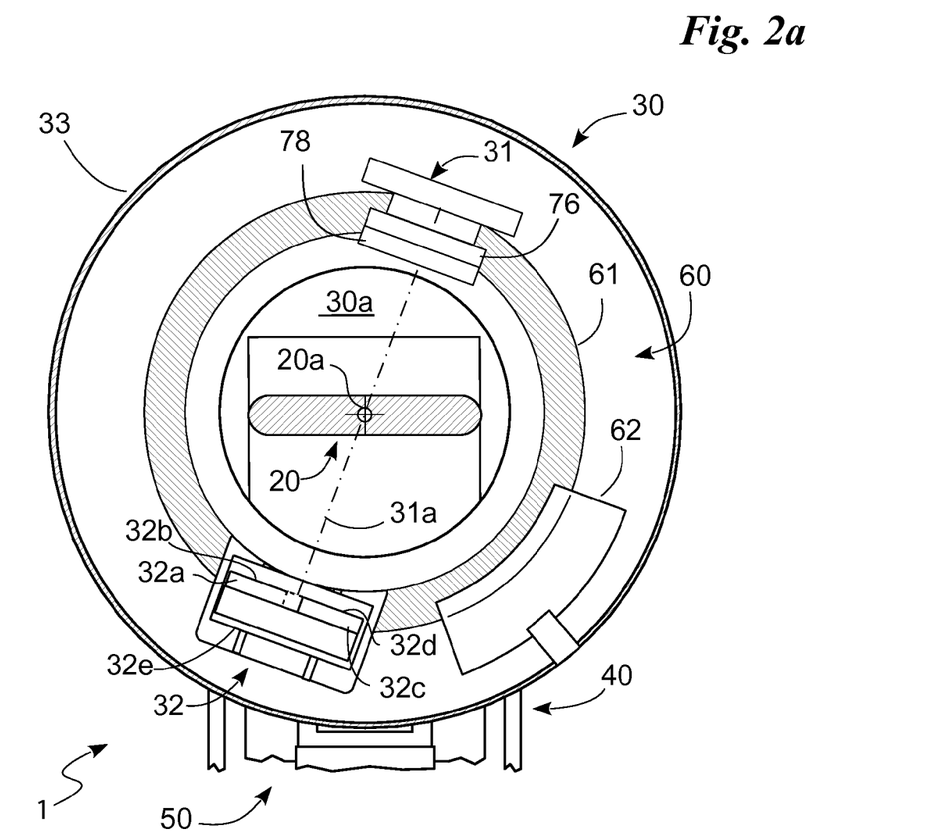
FIG. 2a illustrates a cross-section of an example embodiment of the radiological imaging device of FIG. 1.
Figure 2B:
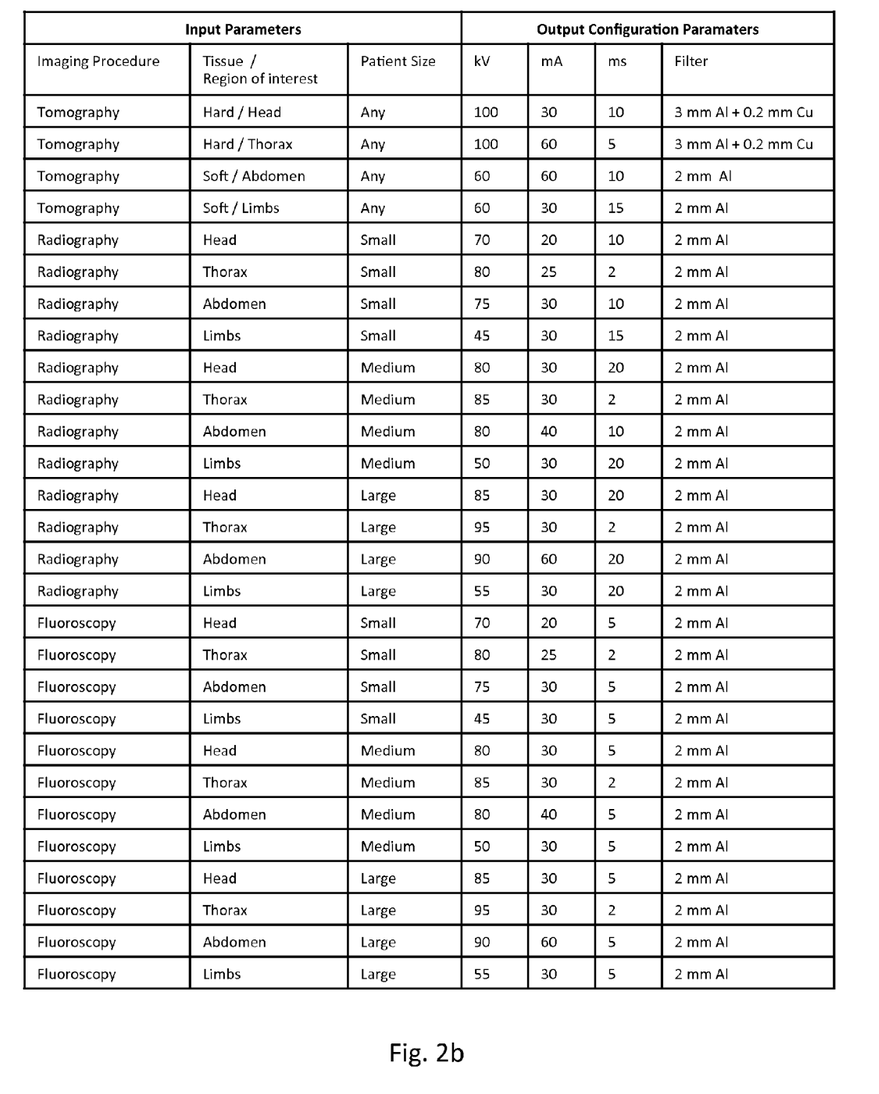
FIG. 2b is a table showing predetermined relationships for configuring an X-ray source according to an example embodiment herein.
Figure 2C:
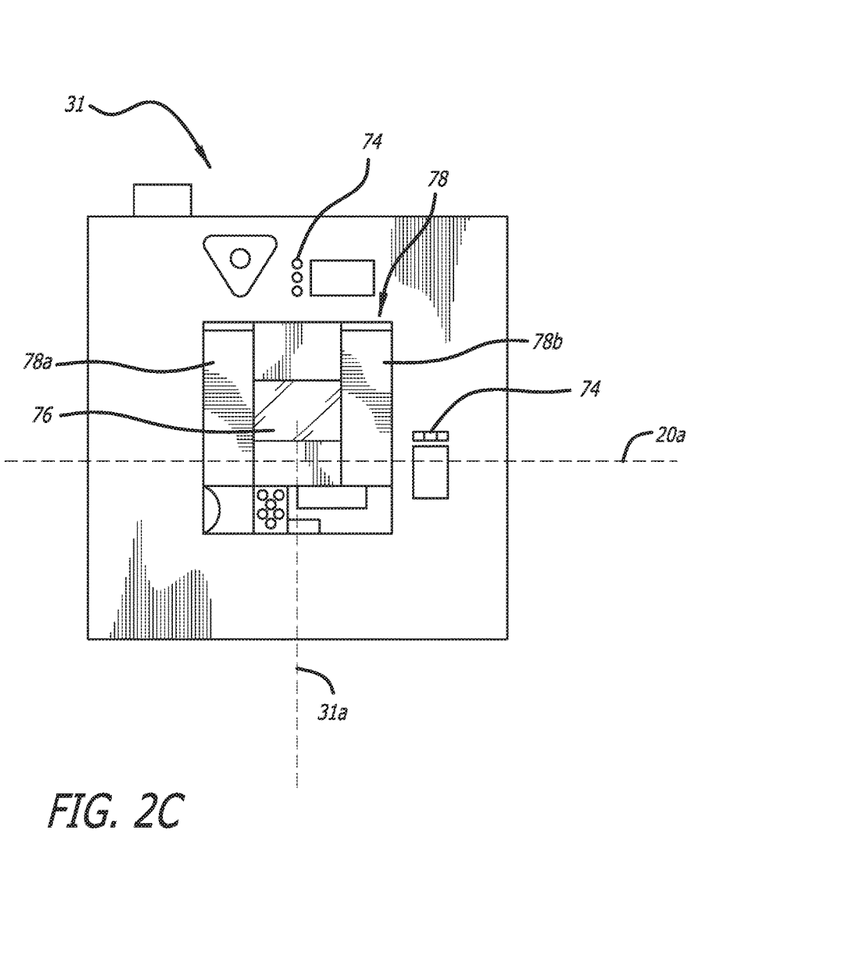
FIG. 2c depicts a source subassembly of the imaging device of FIG. 1 according to an example embodiment herein.

FIG. 2c depicts the source 31 of the radiological imaging device 1 of FIG. 1, according to an example embodiment herein. As represented in FIG. 2a and shown in FIG. 2c, in one example embodiment herein, an X-ray filter 76 can optionally be positioned in front of the source 31, as represented in FIG. 2a and shown in FIG. 2c, and function to modify the energy distribution of the radiation emitted by the source 31 along the axis of propagation 31a (e.g., by absorbing low power X-rays) prior to the X-rays traversing the patient (although source 21 also may be operated without an X-ray filter 76). The X-ray filter 76 may comprise an aluminum and/or copper sheet (or any other material suitable for the absorption of radiation) of predetermined thickness.

In another example embodiment herein, a plurality of X-ray filters (not shown) are stored at different locations in the gantry 30, each of the plurality of X-ray filters differing from others of the filters in terms of at least one of a type of material (such as an aluminum and/or copper sheet) or thickness. The control unit 70 can cause a motorized mechanism (not shown) provided within the gantry 30 to retrieve a selected X-ray filter (e.g., selected by control unit 70 in a manner to be described further herein below) from storage and position the selected X-ray filter in front of the source 31.

In a further example embodiment herein, the operator can operate control unit 70 to input information, such as, for example and without limitation, a type of the imaging procedure selected to be performed (e.g., fluoroscopy, tomography, or radiography), a type of patient species, the patient's weight, and/or tissue type to be imaged, and cause the control unit 70 to automatically configure the radiological imaging device 1 to use an optimal radiation dosage. In response, the control unit 70 determines an X-ray emission energy from the source 31 (X-ray emission energy being a function of parameters including X-ray tube voltage, X-ray tube current, and exposure time) and/or a type of X-ray filter 76 to employ, so that the radiological imaging device 1 can perform the selected imaging procedure with an X-ray dosage that is safe for the patient, as well as the operator, while maintaining optimal image quality.

For example, the control unit 70 can perform the aforementioned determination of X-ray emission energy and/or select an X-ray filter type based on predetermined relationships (e.g., defined in accordance with look-up table(s), conditional statement algorithm(s), and/or mathematical formula(s) implemented on control unit 70, although these examples are not limiting) between the patient information, the radiological imaging procedure selected to be performed, the X-ray emission energy, and the materials and thicknesses of the X-ray filters available in the plurality of X-ray filters located inside the gantry. Examples of such predetermined relationships are shown in the table of FIG. 2b.

As but one non-limiting example, if an operator specifies as input (by way of control unit 70) that high resolution tomography is to be performed on hard tissues (e.g., a thorax region), the control unit 70 determines, via a look up table, for example, that the aforementioned input correlates to operating parameters for the source 31 of 100 kV and 60 mA for 5 ms and an X-ray filter 76 of a type comprising a 3 mm thick sheet of aluminum together with a 0.2 mm thick sheet of copper (see FIG. 2b). As another example, if an operator specifies (by way of the control unit 70) that high resolution tomography is to be performed on soft tissues (e.g., an abdominal region), the control unit 70 determines, via a look-up table, for example, that that input correlates to operating parameters for the source 31 of 60 kV and 60 mA for 10 ms and an X-ray filter 76 of a type comprising a 2 mm thick sheet of aluminum (see FIG. 2b).

In yet another example embodiment herein, the source 31 is selectably configured (e.g., by control unit 70) to emit either a cone-shaped beam of radiation or a fan-shaped beam of radiation, by configuring the shape of an adjustable diaphragm 78. The adjustable diaphragm 78, shown in FIG. 2c, comprises at least two movable plates 78a and 78b capable of substantially blocking radiation, the plates 78a and 78b being movable into at least one of an open configuration or a slit configuration by a motorized mechanism (not shown) under operator control by way of control unit 70. When the adjustable diaphragm 78 is configured in the open configuration, radiation from the source 31 is not blocked and emits along the axis of propagation 31a in the shape of a cone. When the adjustable diaphragm 78 is configured as a slit, a portion of the radiation of the source 31 is blocked, and thus radiation emits along the axis of propagation 31a in the shape of a fan (i.e., a cross-section of the cone-shaped radiation) oriented perpendicularly to the direction of extension 20a. Thus, in one example embodiment herein, an operator may configure the source 31 to emit either a cone-shaped beam or a fan-shaped beam by virtue of the adjustable diaphragm 78, and perform different types of imaging with the radiological imaging device 1, such as, for example, cone beam tomography or fan beam tomography, respectively.

The laser positioning system (including horizontal laser(s) 72 and vertical laser(s) 74 mounted in the gantry 30), when activated on the control unit 70, projects visual markers onto the patient in order to facilitate positioning of the patient on the bed 20, and more particularly, within the analysis zone 30a. In particular, in one example embodiment herein, the laser positioning system is used in conjunction with an adjustable bed (serving as bed 20), according to one or more of the example embodiments described in U.S. Provisional Patent Application Nos. 61/932,034 and 61/944,956, which are incorporated by reference herein in their entireties, as if set forth fully herein. Referring to FIGS. 6a and 6b, which illustrate a gantry 20 according to an example embodiment of the radiological imaging device illustrated in FIG. 1, the laser positioning system includes at least one horizontal laser 72, which projects horizontal visual markers 73 to aid the operator in adjusting the height and inclination of the patient with respect to the gantry 30, and/or at least one vertical laser 74, which projects a top-down marker 75 to aid the operator in adjusting the lateral centering of the patient with respect to the gantry 30. The operator adjusts the position of the patient by observing the position of the patient with respect to the projected laser markers 73 and 75, and thus with respect to the analysis zone 30a, and then, for example, manually repositioning the patient on the bed 20 or by adjusting controls on the aforementioned adjustable bed (not shown in FIGS. 6a and 6b) until the patient is deemed by the operator to be in the correct position for imaging.

Figure 5A:
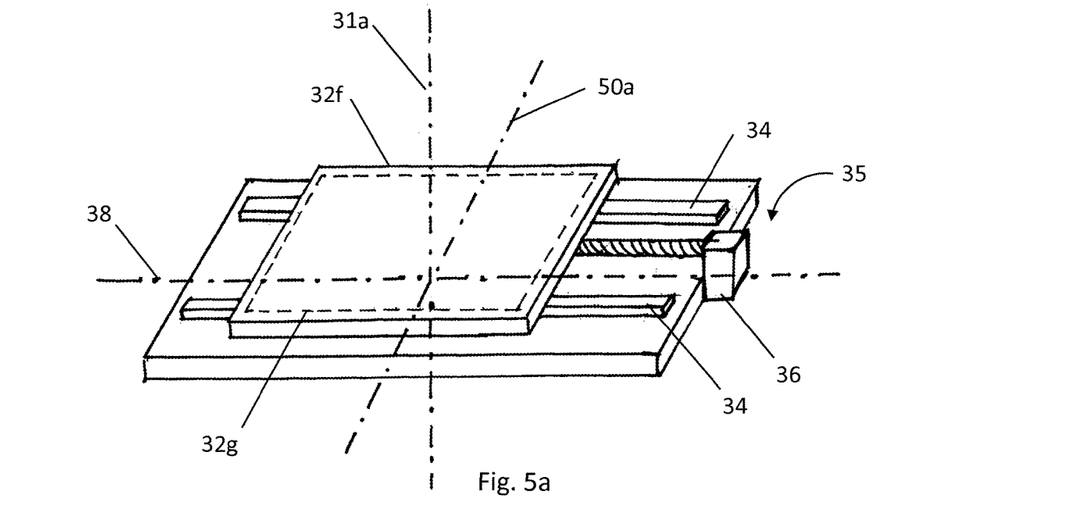
FIG. 5a illustrates a matrix mode of a flat panel sensor subassembly of the imaging device of FIG. 1 according to another example embodiment herein.
Figure 5B:
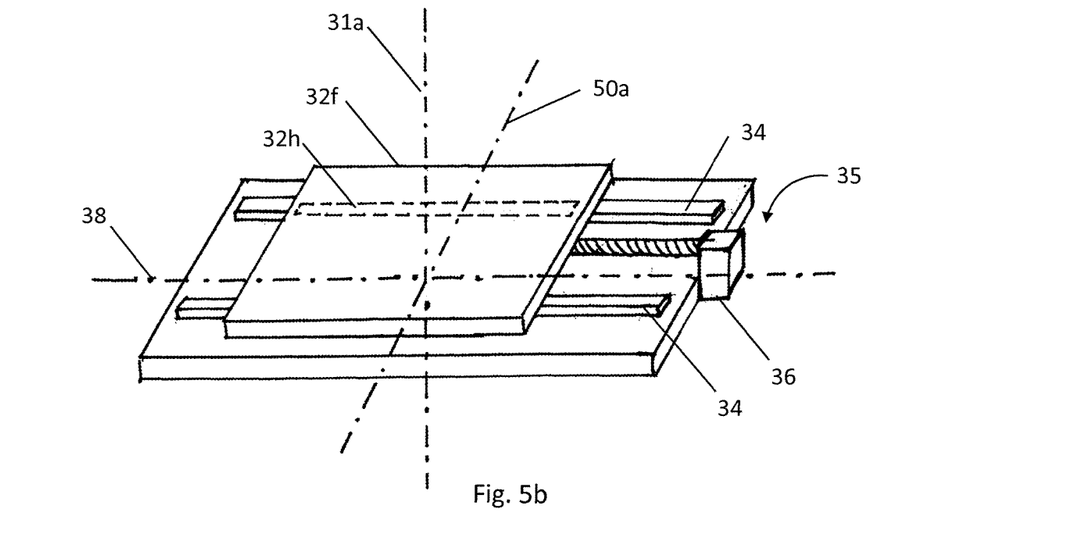
FIG. 5b illustrates a linear sensor mode of a flat panel sensor subassembly of the imaging device of FIG. 1 according to another example embodiment herein.

Referring again to FIG. 2a, the detector 32 will now be described. The detector 32 is suitable for detecting radiation emitted by source 31 and, in response thereto, outputting corresponding data signals to the control unit 70 at a particular frame rate. The control unit 70, in turn, processes the data signals to acquire images. As will be described further herein below, the detector 32 may include either at least one linear sensor (e.g., such as two linear sensors, as illustrated in FIGS. 3a and 3b) or at least one flat panel sensor capable of operating in a linear sensor mode (FIGS. 5a and 5b).

In one example embodiment herein, the detector 32 comprises at least one linear sensor defining a sensitive surface (not shown), that is to say, a surface suitable to detect the radiation emitted by the source 31.

Figure 3A:
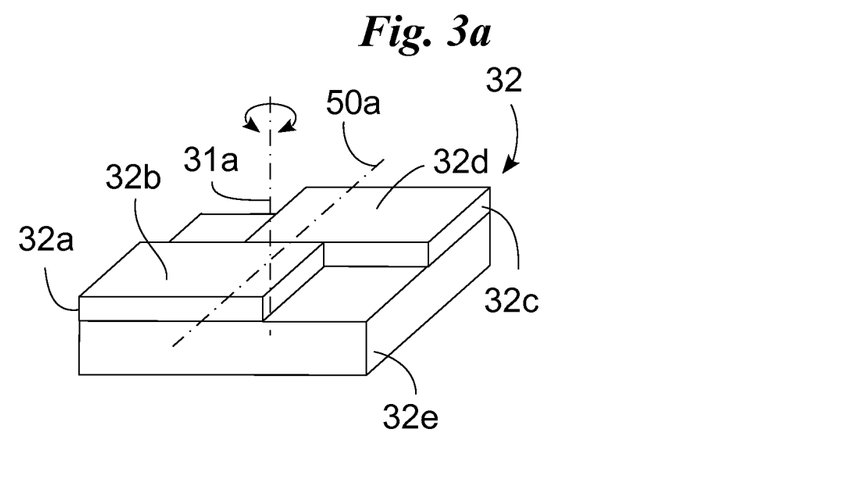
FIGS. 3a and 3b illustrate a detector subassembly of the imaging device of FIG. 1 according to an example embodiment herein.
Figure 3B:
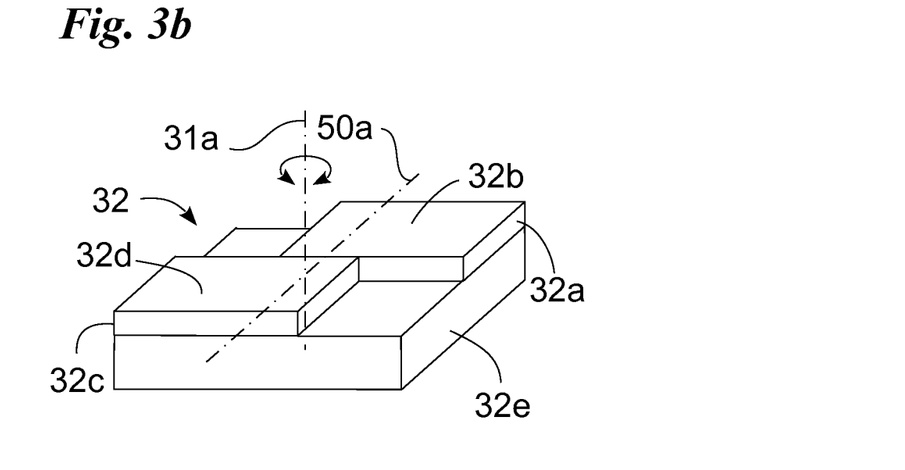

In another example embodiment herein, and with reference to FIGS. 2a, 3a, and 3b, the detector 32 comprises at least a first linear sensor 32a defining a first sensitive surface 32b, and a second linear sensor 32c defining a second sensitive surface 32d. The sensitive surfaces 32b and 32d are suitable for detecting radiation emitted by the source 31. In one example embodiment herein, the second sensitive surface 32d is substantially coplanar with the first sensitive surface 32b, although this example is non-limiting. Preferably, the linear sensors 32a and 32c have a frame rate of, for example, approximately 50 frames per second to approximately 300 frames per second.

As shown in FIGS. 3a and 3b, the sensors 32a and 32c are positioned in such a way as to be in contact with each other and to present the sensitive surfaces 32b and 32d substantially perpendicularly to the central axis of propagation 31a. More precisely, they are positioned so that at least a portion of the first sensitive surface 32b and at least a portion of the second sensitive surface 32d overlap in the direction of movement 50a, so that when the translation mechanism 50 moves the detector 32 along said movement direction 50a, the radiation traversing a defined portion of body hits such portions of the sensitive surfaces 32b and 32d sequentially and substantially without interruption (that is to say, in such a way that the radiation passes practically directly from the portion of the first surface 32b to that of the second 32d). The aforementioned overlapping portions of the sensitive surfaces 32b and 32d are positioned substantially at the axis of propagation 31a.

In particular, the linear sensors 32a and 32c have sensitive surfaces 32b and 32d substantially equal to each other in size and are, in relation to the direction of movement 50a, overlapping so that the fraction of the sensitive surfaces 32b and 32d suitable to be sequentially hit by the radiation as the gantry 30 is moved by translation mechanism 50 is substantially less than 30% and particularly, substantially less than 20%, and more particularly, substantially less than 10%.

Figure 4:
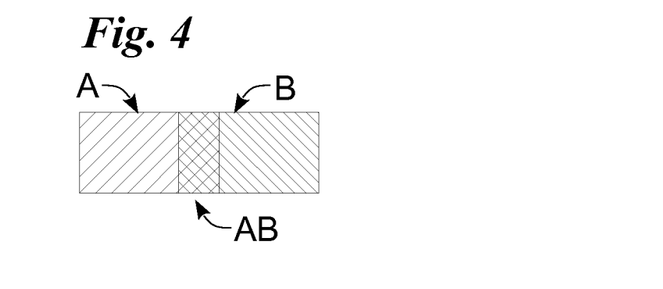
FIG. 4 illustrates images acquired by the detector subassembly of FIGS. 3a and 3b.

A high quality image can be generated from two separate linear sensors 32a and 32c by virtue of their overlap, as will now be described, by way of example, with reference to FIG. 4. FIG. 4 illustrates a representation of a first image "A" acquired by the first sensor 32a and a second image "B" acquired by the second sensor 32c. The images "A" and "B" partially overlap in a region "AB" where the first and second sensors 32a and 32c overlap.

Edge effects that may cause image degradation in corresponding edge regions of acquired images are minimized by virtue of reconstructing a single image from the overlapping images "A" and "B" according to an example embodiment herein. For example, the control unit 70 can reconstruct an image by combining portions of images "A" and "B", including a portion of image "A" that overlaps an edge of sensor 32c and a portion of image "B" that overlaps an edge of sensor 32a, but excluding a portion of image "B" that corresponds to the edge of sensor 32c and portion of image "A" that corresponds to the edge of sensor 32a (i.e., excluding those portions where images "A" and "B" may manifest undesirable edge effects of the first and second sensors 32a and 32c, respectively). Accordingly, the radiological image device 1 is capable of reconstructing an image from two linear sensors while minimizing edge effects or other reconstruction errors resulting from the edges of the sensors 32a and 32c in the overlapping region, and high quality scans of a patient's body can be obtained, including areas of radiological interest in the patient's body scanned in the overlapping region.

Referring again to FIGS. 2a, 3a, and 3b, the example embodiment of detector 32 using linear sensors 32a and 32c also can comprise an inversion unit 32e suitable to rotate at least one of the linear sensors 32a and 32c about a substantially non-perpendicular axis of rotation and, specifically, about an axis substantially parallel to the central axis of propagation 31a, so as to invert the direction of reading. In particular, the inversion unit 32e simultaneously rotates both sensors 32a and 32c substantially in relation to the central axis of propagation 31a, for example, by an angle substantially equal to 180° so as to invert the order of the linear sensors 32a and 32c in relation to the direction of movement 50a as shown in FIGS. 3a and 3b.

Alternatively, the inversion unit 32e can move the sensors 32a and 32c independently of each other. In particular, the inversion unit 32e moves the first linear sensor 32a by means of a roto-translational movement, that is, more precisely, a translational movement along a direction of movement 50a, and a rotational movement about an axis of rotation parallel to the central axis 31a of an angle substantially equal to 180°. Practically simultaneously to said roto-translational movement of the first linear sensor 32a, the inversion unit 32e rotates the second linear sensor 32c about an axis of rotation separate from the axis of rotation of the first linear sensor 32a and substantially parallel to the axis 31a. Alternatively, the inversion unit 32e roto-translates the second linear sensor 32c along an axis substantially parallel to the axis of the roto-translation of the first linear sensor 32a.

Another example embodiment of the detector 32 will now be described. In this embodiment, the detector 32 comprises at least one flat panel sensor 32f (as shown in FIGS. 5a and 5b), that includes an array of pixels and is capable of operating in a selected one of multiple independent read-out modes, selectable by control unit 70, including at least a matrix mode (FIG. 5a) and a linear sensor mode (FIG. 5b).

In the matrix mode (FIG. 5a), the flat panel sensor 32f outputs, to control unit 70, signals corresponding to radiation detected by pixels in a region of sensitive surface 32g. In one example embodiment herein, the sensitive surface 32g is substantially coextensive with the entire array of pixels of the flat panel sensor 32f.

In the linear sensor mode (FIG. 5b), the flat panel sensor 32f outputs, to control unit 70, signals corresponding to radiation detected by the subset of pixels in a region of sensitive surface 32h. The sensitive surface 32h functions effectively as a linear sensor (e.g., in a manner similar to linear sensors 32a and 32c); that is, in one example, the sensitive surface 32h has a frame rate in the range of approximately 50 frames per second to approximately 300 frames per second and has a width that is substantially greater than its length, its length being defined in a direction substantially parallel to direction 50a and its width being defined substantially perpendicular to the direction of movement 50a and the central axis of propagation 31a.

The pixel array size of sensitive surfaces 32g and 32h can be predefined for the flat panel sensor 32f in hardware, firmware, software, or other means by which the flat panel sensor 32f may be controlled.

In particular, in one example embodiment herein, the flat panel sensor 32f may be a Hamamatsu model C11701DK-40 flat panel sensor, which can operate in a matrix mode that provides a sensitive surface 32g, having a 1096×888 array of pixels or a 2192×1776 array of pixels, and can also separately operate in a linear sensor mode that provides a sensitive surface 32h, having a 1816×60 array of pixels.

Additionally, the flat panel sensor 32f can be mounted on a panel motion system 35 that includes guides 34 and a motorized translation mechanism 36 (FIGS. 5a and 5b). The panel motion system 35 is suitable for moving the flat panel sensor 32f along an axis 38, which is substantially perpendicular to both the gantry direction of movement 50a and the central axis of propagation 31a. In particular, the axis 38 is also parallel to the width of the sensitive surface 32h when the flat panel sensor 32f is operating in the linear sensor mode. Accordingly, owing to the panel motion system 35, the flat panel sensor 32f can be operated to acquire a plurality of scans, each at different but overlapping locations along the axis 38 (although this example is non-limiting), as will be described further herein below with reference to the procedures described in FIG. 7.

Having described various example embodiments of the detector 32, the translation mechanism 50 and rotation mechanism 60 of the radiological imaging device 1 will now be discussed, with reference to FIG. 1.

The translation mechanism 50 is suitable to translate, at the same time, at least the detector 32 and the source 31 and, in particular, the entire gantry 30, in relation to the load-bearing structure 40 along the direction of movement 50a, so as to permit the radiological imaging device 1 to perform radiological imaging over practically the entire extension of the bed 20 and therefore the patient. In particular, the direction of movement 50a is substantially perpendicular to the central axis of propagation 31a, and more particularly, substantially parallel to the preferred direction of extension 20a. The translation mechanism 50 comprises a linear guide 51 positioned between the gantry 30 and the load-bearing structure 40 and a carriage 53, attached to the gantry 30, suitable to slide along the linear guide 51. In an example embodiment herein, the linear guide 51 may be a motorized linear guide or, more specifically, an electric motorized linear guide. Preferably, the translation mechanism 50 is able to move the gantry 30 and, therefore, the detector 32 and the source 31, at a speed, for example, in the range of approximately 2.5 meters per second to approximately 100 meters per second. Additionally, the translation of the gantry 30 by the translation mechanism 50 can be controlled by the control unit 70.

In addition to the translation mechanism 50, the radiological imaging device 1 comprises a rotation mechanism 60 (FIG. 2a) suitable to rotate the source 31 and the detector 32 with respect to an axis substantially parallel to the direction of movement 50a and, in detail, substantially coincident to said preferred direction of extension 20a. The rotation mechanism 60 is housed inside the gantry 30 and, in particular, inside the housing 33 so as to rotate the source 31 and the detector 32 in relation to said housing 33. In one example embodiment, the rotation mechanism 60 comprises a rotor 61, such as a permanent magnet rotor, to which the source 31 and the detector 32 are connected; and a stator 62 integrally connected to the housing 33 and suitable to emit a magnetic field controlling the rotation of the rotor 61, and thereby, of the source 31 and the detector 32. Operation of the rotation mechanism 60 can be controlled by control unit 70.

Figure 8:
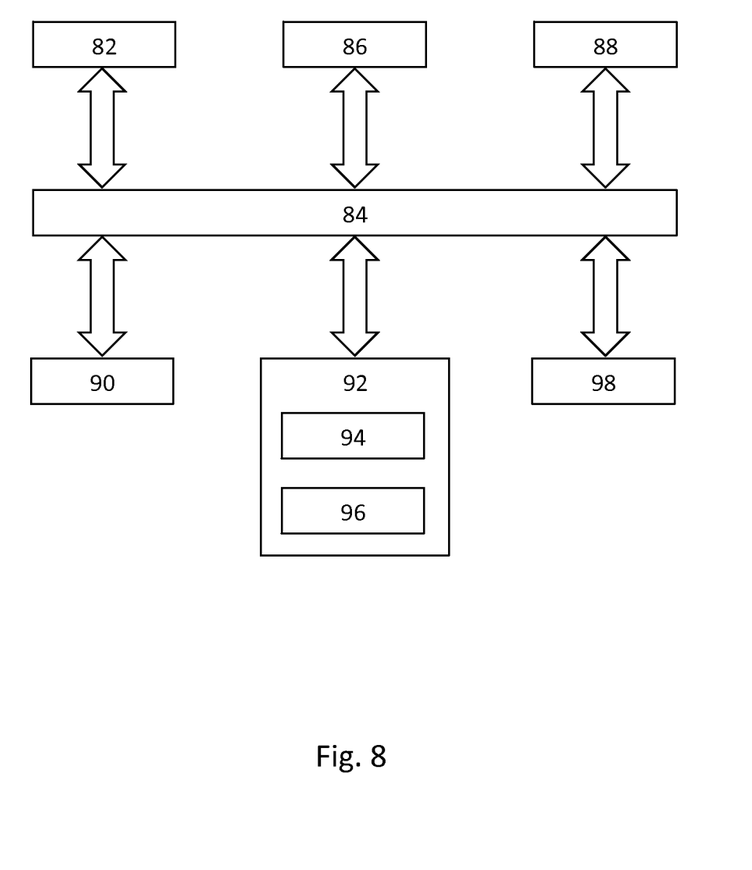
FIG. 8 illustrates a block diagram of an example computer system of the radiological imaging system shown in FIG. 1.

FIG. 8 illustrates a block diagram of a computer system 80. In one example embodiment herein, at least some components of the computer system 80 can form or be included in the aforementioned control unit 70, and computer system 80 is electrically connected to other components of the radiological imaging device 1 (such as, for example, the source 31, the detector 32, the gantry 30, and any subcomponents thereof) by way of communications interface 98 (mentioned below). The computer system 80 includes at least one computer processor 82 (also referred to as a "controller"). The computer processor 82 may include, for example, a central processing unit, a multiple processing unit, an application-specific integrated circuit ("ASIC"), a field programmable gate array ("FPGA"), or the like. The processor 82 is connected to a communication infrastructure 84 (e.g., a communications bus, a cross-over bar device, or a network). Although various embodiments are described herein in terms of this exemplary computer system 80, after reading this description, it will become apparent to a person skilled in the relevant art(s) how to implement the invention using other computer systems and/or architectures.

The computer system 80 may also include a display unit 86 for displaying video graphics, text, and other data provided from the communication infrastructure 84. In one example embodiment herein, the display unit 86 can form or be included in the control unit 70.

The computer system 80 also includes an input unit 88 that can be used by the operator to send information to the computer processor 82. For example, the input unit 88 can include a keyboard device and/or a mouse device or other input device(s). In one example, the display unit 86, the input unit 88, and the computer processor 82 can collectively form a user interface.

In an example embodiment that includes a touch screen, for example, the input unit 88 and the display unit 86 can be combined. In such an embodiment, an operator touching the display unit 86 can cause corresponding signals to be sent from the display unit 86 to a processor such as processor 82, for example.

In addition, the computer system 80 includes a main memory 90, which preferably is a random access memory ("RAM"), and also may include a secondary memory 92. The secondary memory 92 can include, for example, a hard disk drive 94 and/or a removable storage drive 96 (e.g., a floppy disk drive, a magnetic tape drive, an optical disk drive, a flash memory drive, and the like) capable of reading from and writing to a corresponding removable storage medium, in a known manner. The removable storage medium can be a non-transitory computer-readable storage medium storing computer-executable software instructions and/or data.

The computer system 80 also can include a communications interface 98 (such as, for example, a modem, a network interface (e.g., an Ethernet card), a communications port (e.g., a Universal Serial Bus ("USB") port or a FireWire® port), and the like) that enables software and data to be transferred between the computer system 80 and external devices. For example, the communications interface 98 may be used to transfer software or data between the computer system 80 and a remote server or cloud-based storage (not shown). Additionally, the communication interface 98 may be used to transfer data and commands between the computer system 80 (serving as control unit 70) to other components of the radiological imaging device 1 (such as, for example, the source 31, the detector 32, the gantry 30, and any subcomponents thereof).

One or more computer programs (also referred to as computer control logic) are stored in the main memory 90 and/or the secondary memory 92 (i.e., the removable-storage drive 96 and/or the hard disk drive 94). The computer programs also can be loaded into the computer system 80 via the communications interface 98. The computer programs include computer-executable instructions which, when executed by the controller/computer processor 82, cause the computer system 80 to perform the procedures described herein and shown in at least FIG. 7, for example. Accordingly, the computer programs can control the control unit 70 and other components (e.g., the source 31, the detector 32, the gantry 30, and any subcomponents thereof) of the radiological imaging device 1.

Figure 7:
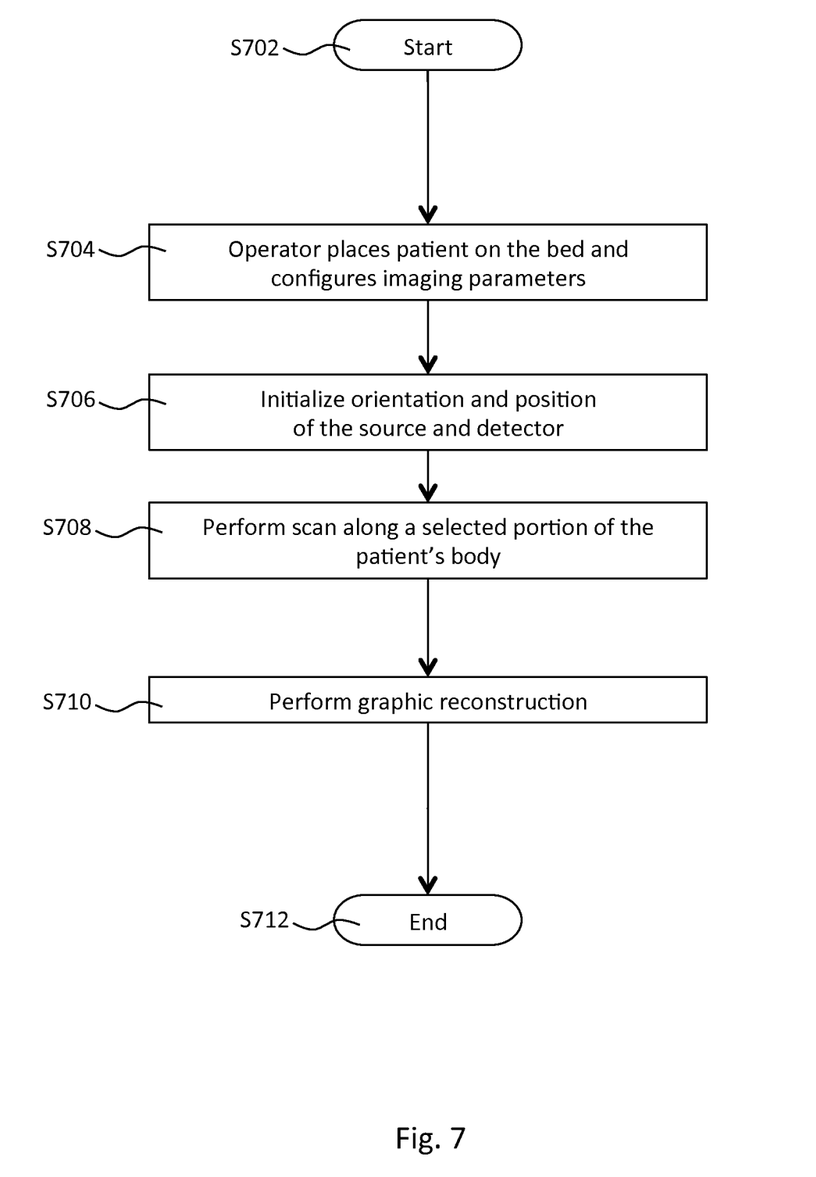
FIG. 7 is a flowchart illustrating an imaging procedure according to an example embodiment herein.

A procedure for imaging at least a portion of a patient using the radiological imaging device that was described above in a structural sense, will now be further described in conjunction with FIG. 7. The process starts in Step S702.

Initially, in Step S704, the operator places the patient on the bed 20. In one example embodiment herein, the operator activates the laser positioning system (comprising lasers 72 and 74, as shown in FIGS. 6a and 6b), which projects horizontal visual markers 73 to assist the operator in adjusting the height and inclination of the patient with respect to the gantry 30, and/or projects a top-down marker 75 to assist the operator in laterally adjusting the patient with respect to the gantry 30.

Also in Step S704, the operator operates the control unit 70 to specify imaging parameters, such as the portion of body on which to perform a total body scan (also referred to as the zone to be imaged) and, in particular, the inclination of the central axis of propagation 31a and the travel of the gantry 30, that is to say the advancement of the gantry 30 along the preferred direction of extension 20a. The operator also may operate the control unit 70 to input patient information (e.g., species, weight, and/or tissue type to be imaged), and may further command the control unit 70 to automatically configure the radiological imaging device 1 to select an appropriate radiation dose based on the patient information, in the above described manner.

Then, in Step S706, the control unit 70 responds to the aforementioned operator specified imaging parameters and controls the rotation mechanism 60 so as to rotate the source 31 and the detector 32 in order to orient the central axis of propagation 31a in relation to the bed 20, and therefore to the patient. Additionally, if the operator commanded the control unit 70 to automatically configure the radiological imaging device 1 to use an appropriate radiation dose in Step S704, the control unit 70 configures the X-ray source 31 and the X-ray filter 76 in the manner described above, so as to be prepared to provide such a dosage. Once the central axis of propagation has reached the desired inclination, scanning commences in Step S708.

Step S708 will now be described. During scanning in Step S708, the translation mechanism 50 moves the gantry 30 along the preferred direction of extension 20a so that the source 31 and the detector 32 translate together in relation to the bed 20 and to the patient, thereby permitting the radiation to scan the entire zone to be imaged. Simultaneously to the aforementioned translation action, the source 31 emits radiation, which, after traversing the patient's body, is detected by the detector 32, which in turn sends a suitable signal to the control unit 70.

The manner in which Step S708 is performed in a case where the detector 32 comprises two linear sensors 32a and 32c will now be described. As the gantry 30 advances in the direction of movement 50a, the source 31 emits radiation, which, after traversing the patient's body, hits the first sensitive surface 32b and, practically simultaneously, hits the second sensitive surface 32d. More particularly, each part of the portion of the body being scanned is first scanned by the portion of the first surface 32b corresponding to the first sensor 32a part in contact with the second sensor 32c, and subsequently, is scanned by the portion of the second surface 32d adjacent to the previous portion. The linear sensors 32a and 32c detect the radiation and send a continuous signal to the control unit 70, which thus receives a single signal for the zone to be imaged and processes the signal to acquire an image of the scanned part of the patient.

In some situations, the operator may have selected, in Step S704, a direction of translation of the gantry 30 for imaging that is a reverse direction relative to the orientation of the sensors 32a and 32c, which may result in the data output order of the sensors 32a and 32c being reversed. That is, as the radiological imaging device 1 is translated and the source 31 is controlled to emit radiation, radiation is first detected by the second sensor 32c before being detected by the first sensor 32a (see, for example, FIG. 3b). In order to acquire the data output in a non-reverse order, in a further example embodiment herein, performing Step S708 using the linear sensors 32a and 32c also may include a preliminary substep (i.e., that is performed prior to the above-described scanning in Step S708) of controlling the inversion unit 32e, either manually by the operator or automatically by the control unit 70, so as to rotate the sensors 32a and 32c about an angle substantially equal to 180° in relation to the central axis of propagation 31a. By virtue of the preliminary substep, the order of the sensors 32a and 32c can be inverted in relation to the direction of movement 50a so that radiation would first be detected by the first sensor 32a prior to being detected by the second sensor 32c (see, for example, FIG. 3a in comparison to FIG. 3b).

Having described scanning in Step S708 using the linear sensors 32a and 32c, scanning in Step S708 in the case where the detector 32 comprises a flat panel sensor 32f (versus sensors 32a and 32c) operating in a linear sensor mode with sensitive surface 32h (FIG. 5b) will now be described.

During a scan, the source 31 continuously emits radiation, which traverses the patient's body and hits the sensitive surface 32h of flat panel sensor 32f. As the gantry 30 advances in the direction of movement 50a, the flat panel sensor 32f detects radiation during such movement and sends corresponding signals to the control unit 70. Accordingly, the control unit 70 receives a signal for the entire zone to be imaged and processes the signal to acquire an image of the scanned part of the patient.

Additionally, if desired by the operator, one or more additional scans may be performed. For each additional scan, the flat panel sensor 32f can be translated along axis 38 by the panel motion system 35 (under control of control unit 70) to a new position that partially overlaps the position of the flat panel sensor 32f in a previous scan, and more particularly, the immediately preceding scan. Then, a further scanning procedure is performed in the manner described above, that is, the gantry 30 advances in the direction of movement 50a while the source 31 emits radiation and the flat panel sensor 32f continuously outputs a signal to the control unit 70. In this manner, a plurality of scans can be acquired, each scan being as wide as the sensitive surface 32h and as long as the travel of gantry 30 along the direction of movement 50a. The plurality of scans is then provided to the control unit 70 for graphic reconstruction in Step S710.

Next, in Step S710, the control unit 70 carries out the graphic reconstruction of the zone being imaged using the readings performed by the detector 32. In the example embodiment where detector 32 comprises two linear sensors 32a and 32c, overlapping images from first and second detectors 32a and 32c are reconstructed in the manner described above, with reference to FIG. 4.

In the example embodiment where detector 32 comprises flat panel sensor 32f operating in the linear sensor mode, the plurality of scans acquired in Step S708 by flat panel sensor 32f operating in the linear sensor mode can be reconstructed into one overall image in a manner that minimizes edge effects in overlapping regions of the plurality of images, similar to the manner of reconstruction discussed above with respect to the two linear sensors 32a and 32c (see FIG. 4). Thus, by virtue of the panel motion system 35, the flat panel sensor 32f can provide an overall radiological image that is wider than the sensitive surface 32h.

The process ends at step S712. The operator may repeat the process or a portion thereof to acquire additional scans, as desired.

In view of the foregoing description, it can be appreciated that at least some example embodiments described herein provide a radiological imaging device 1 that produces high quality total body scan images.

In fact, the use of the linear sensors 32a and 32c or the flat panel sensor 32f functioning as a linear sensor, together with the translation mechanism 50, makes it possible to perform continuous data acquisition and, consequently, to innovatively obtain a reconstruction based on a continuous scan of the portion of the body analyzed, rather than by the approximation from a number of discrete two-dimensional images, as is the case with the prior art radiological imaging devices.

Additionally, by virtue of the partial superimposition of the linear sensors 32a and 32c in the example embodiment of detector 32 using those sensors, it is possible to obtain a low cost detector 32 with a considerably extensive effective sensitive surface, being defined by the combination of the surfaces 32b and 32d. Similarly, in the example embodiment of detector 32 employing the flat panel sensor 32f, by virtue of mounting the flat panel sensor 32f on the panel motion system 35, it is possible to capture high quality images that are larger than the flat panel sensor 32f.

Furthermore, the radiological imaging device 1 exposes the patient and operator to a reduced dosage relative to the case of prior art systems. In particular, the use of the linear sensors 32a and 32c or the flat panel sensor 32f functioning as a linear sensor makes it possible to not use the anti-diffusion grids and thereby, to reduce the necessary intensity of the radiation emitted by the source 31.

According to at least some example embodiments herein, the radiological imaging device makes it possible to further limit the patient's exposure to radiation. As described above, total body imaging with a flat panel sensor that conventionally has to overlap a number of two-dimensional images may irradiate some parts of the body twice or more. As a result, the patient is exposed to a conspicuous amount of radiation. In contrast to such conventional methods, scanning with radiological imaging device 1 can be performed with a reduced emission of radiation by virtue of the use of a detector 32 comprising linear sensors 32a and 32c or the flat panel sensor 32f functioning as a linear sensor, and continuously translating the detector 32 along the direction of movement 50a without overlapping any part of the body in the course of a single scan.

Moreover, in the example embodiment where detector 32 comprises two linear sensors 32a and 32c, the presence of the inversion unit 32e makes it possible to carry out radiological imaging in both sliding directions of the gantry 30 along the direction of movement 50a by permitting inversion of the order of the linear sensors 32a and 32c in relation to the direction 50a.

Also, by virtue of the radiological imaging device 1, it is possible to perform total body scanning at 360° and along the entire length of the bed 20.

The various embodiments described above have been presented by way of example and not limitation. It will be apparent to persons skilled in the relevant art(s) that various changes in form and detail can be made therein (e.g., different hardware, communications protocols, materials, shapes and dimensions) without departing from the spirit and scope of the present invention. Thus, the present invention should not be limited by any of the above-described exemplary embodiments, but should be defined only in accordance with the following claims and their equivalents.

In addition, it should be understood that the attached drawings, which highlight functionality described herein, are presented as illustrative examples. The architecture of the present invention is sufficiently flexible and configurable, such that it can be utilized (and navigated) in ways other than that shown in the drawings.

Further, the purpose of the appended Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way.

What is claimed:

1. A radiological imaging device comprising:
   a gantry defining an analysis zone in which at least part of a patient is placed;
   a source suitable to emit radiation that passes through the at least part of the patient, the radiation defining a central axis of propagation;
   a detector suitable to receive the radiation, and the detector includes a single flat panel sensor having a radiation sensitive surface and operable in at least a flat panel mode and a linear sensor mode;
   a panel motion system connected to the detector, the panel motion system suitable for moving the detector along an axis perpendicular to the central axis of propagation;
   a translation mechanism adapted to translate the source and the detector in a direction of movement substantially perpendicular to the central axis of propagation;
   a control unit adapted to acquire an image from data signals received continuously from the detector while the translation mechanism continuously translates the source emitting the radiation and the detector receiving the radiation, so as to scan the at least part of the patient;
   a bed suitable to support the patient and defining an axis of extension; and
   a rotation mechanism adapted to rotate the source and the detector in relation to the axis of extension.

2. The radiological imaging device according to claim 1, wherein the direction of movement is substantially parallel to the axis of extension.

3. The radiological imaging device according to claim 1, wherein the rotation mechanism includes a permanent magnet rotor connected to the source and to the detector.

4. The radiological imaging device according to claim 1, wherein the translation mechanism includes a linear guide.

5. The radiological imaging device according to claim 1, further comprising:
   at least one positioning laser mounted on the gantry that projects a positioning guidance marker onto the patient,
   wherein the control unit is adapted to configure, based on received information, at least one of an energy of the radiation and a radiation filter arranged to absorb at least a portion of the radiation before the radiation passes through the at least part of the patient.

6. A method of acquiring a radiological image of at least part of a patient placed in a gantry, the method comprising:
   providing a bed suitable to support the patient, wherein the bed defines an axis of extension;

causing a source to emit radiation that passes through the at least part of the patient, the radiation defining a central axis of propagation;

rotating the source and the detector in relation to the axis of extension;

receiving the radiation at a detector, and the detector includes a single flat panel sensor and having a radiation sensitive surface and operable in at least a flat panel mode and a linear sensor mode;

moving the detector along guides of a panel motion system along an axis perpendicular to the central axis of propagation;

outputting data signals from the detector to a control unit;

continuously translating the source and the detector in a direction of movement substantially perpendicular to the central axis of propagation; and acquiring, at the control unit, an image from data signals received continuously from the detector while the translation mechanism continuously translates the source emitting the radiation and the detector receiving the radiation, so as to scan the at least part of the patient.

7. The method according to claim 6, wherein the direction of movement is substantially parallel to the axis of extension.

8. The method according to claim 6, wherein the rotating the source and the detector is performed by a rotation mechanism that includes a permanent magnet rotor connected to the source and to the detector.

9. The method according to claim 6, wherein the translation mechanism includes a linear guide.

10. The method according to claim 6, further comprising:

projecting onto the patient at least one positioning guidance marker from at least one positioning laser mounted on the gantry; and configuring, based on information received at the control unit, at least one of an energy of the radiation and a radiation filter arranged to absorb at least a portion of the radiation before the radiation passes through the at least part of the patient.

* * * * *